United States Patent [19]

Dockner et al.

[11] Patent Number: 4,822,918

[45] Date of Patent: Apr. 18, 1989

[54] REDUCTION OF ORGANIC SULFUR COMPOUNDS

[75] Inventors: Toni Dockner, Meckenheim; Manfred Sauerwald, Roedersheim-Gronau, both of Fed. Rep. of Germany

[73] Assignee: BASF Aktiengesellschaft, Ludwigshafen, Fed. Rep. of Germany

[21] Appl. No.: 92,888

[22] Filed: Sep. 4, 1987

[30] Foreign Application Priority Data

Sep. 12, 1986 [DE] Fed. Rep. of Germany ....... 3631073

[51] Int. Cl.$^4$ ................. C07C 149/30; C07C 149/28; C07C 149/06
[52] U.S. Cl. ........................................ 568/58; 568/60; 568/67; 568/69
[58] Field of Search ........................ 568/67, 69, 58, 60

[56] References Cited

U.S. PATENT DOCUMENTS

| | | | |
|---|---|---|---|
| 2,506,416 | 5/1950 | Gilbert et al. | 568/67 |
| 4,278,816 | 7/1981 | Shim | 568/67 |
| 4,284,817 | 8/1981 | Shim et al. | 568/67 |

OTHER PUBLICATIONS

K. Fujimoto, K. Masamizu, S. Asaoka, T. Kunugi: Nippou Kagaku Kaishi 1976, 1067.
Ullmanns Encyklopädie der Technischen Chemie, 4th Ed., vol. 23, (1983), p. 188 and translation.
Houben-Weyl, Methoden der Organischen Chemie, vol. 4/1c, (1980), pp. 486-489 and translation.
Houben-Weyl, Methoden der Organischen Chemie, vol. 9, pp. 23-33, 1955.
Houben-Weyl, Methoden der Organischen Chemie, vol. 4/1c, pp. 486-489, 664-667, 1980.
Houben-Weyl, Methoden der Organischen Chemie, vol. 4/1d, pp. 680-681, 1981.
Houben-Weyl, Methoden der Organischen Chemie, vol. E 11/1, pp. 48-54, 1985.
K. Habashi, Yuki Gosei Kagaku Kyokai Shi 19, pp. 266, 271 and 601, 1967.
Y. Drabowicz, T. Numata and S. Oae, Org. Prep. Proc. Int. 9, p. 64 1977.

*Primary Examiner*—Mary E. Ceperley
*Attorney, Agent, or Firm*—John H. Shurtleff

[57] ABSTRACT

Organic sulfur compounds, such as sulfonic acids, sulfonyl halides, sulfonates, sulfonamides, sulfonic acid anhydrides, sulfones, sulfoxides and/or disulfanes, are reduced by a method in which the sulfur compound in the liquid or gas phase is reacted with a hydrocarbon in the presence of carbon at from 100° to 500° C.

14 Claims, No Drawings

REDUCTION OF ORGANIC SULFUR COMPOUNDS

The present invention relates to a novel process for the reduction of organic sulfur compounds, such as sulfonic acids, sulfonyl halides, sulfonates, sulfonamides, sulfonic acid anhydrides, sulfones, sulfoxides and/or disulfanes.

Houben-Weyl, Methoden der organischen Chemie, Vol. 9, pages 23-33, 1955, Vol. 4/1c, pages 486-489 and 664-667, 1980, Vol. 4/1d, pages 680 and 681, 1981, and Vol. E 11/1, pages 48-54, 1985, describe numerous methods for the reduction of organic sulfur compounds. Particularly noteworthy in this context is the catalytic hydrogenation in the presence of metal catalysts, which is problematic in that sulfanes, disulfanes, mercaptans and thiophenols are strong catalyst poisons, so that a long reaction time or the use of large amounts of catalyst is necessary.

Usable catalysts for the reduction of aromatic sulfonic acid derivatives are sulfides of cobalt, molybdenum, iron or nickel (cf. Ullmanns Encyklopädie der technischen Chemie, 4th Edition, Vol. 23, pages 175-215, in particular page 188, Weinheim, 1983). However, the reduction has to be carried out using pressures of about 100 bar, which requires complicated apparatus. In order to avoid losses of yield in the reduction of sulfonyl chlorides as a result of partial hydrolysis by water of reaction, the reaction must be carried out in the presence of a base, such as calcium oxide or magnesium oxide. The less reactive sulfonic acids cannot be reduced by these processes. At 100°-200° C., the reaction products formed are the corresponding mercaptans or thiophenols, while a further increase in temperature gives hydrocarbons (K. Itabashi, Yuki Gosei Kagaku Kyokai Shi 19 (1961), 601 and K. Itabashi, Yuki Gosei Kagaku Kyokai Shi 19 (1961), 266 and 271).

In addition to the catalytic hydrogenation, another suitable method for the preparation of thiols from sulfonyl chlorides and disulfanes is the reduction with iron, zinc or tin in glacial acetic acid, hydrochloric acid or sulfuric acid. This process has the problem that fairly large amounts of ecologically unacceptable metal salts are produced and have to be worked up appropriately. Another disadvantage is that it is possible to reduce only the reactive derivatives or the sulfonic acids, but not the sulfonic acids themselves.

In addition to the stated processes, a number of other methods are available; an overview of the reduction of sulfones and sulfoxides is given by, for example, J. Drabowicz, T. Numata and S. Oae in Org. Prep. Proc. Int. 9 (1977), 64. However, none of these methods is very suitable for reactions on an industrial scale since either byproducts, such as metal salts or wastewaters, which pollute the environment and are contaminated with salts or sulfur compounds are produced or, on the other hand, reducing agents which are expensive and difficult to handle, such as lithium aluminum hydride, are used.

The prior art furthermore discloses that sulfur dioxide can be reacted with isopentane at from 400° to 500° C. over active carbon to give hydrogen sulfide and sulfur (K. Fujimoto, K. Masamizu, S. Asaoka and T. Kunugi, Nippon Kagaku Kaishi 1976, 1062).

It is an object of the present invention to provide a process for the reduction of organic sulfonic acids, sulfonic acid derivatives, sulfones, sulfoxides and disulfanes which is widely applicable and cheap, overcomes the disadvantages described for the known processes, is distinguished by high selectivities and in particular can be used on a large industrial scale.

We have found that this object is achieved by a process for the reduction of organic sulfur compounds, such as sulfonic acids, sulfonyl halides, sulfonates, sulfonamides, sulfonic acid anhydrides, sulfones, sulfoxides and/or disulfanes (formerly called disulfides) to form mercaptans or sulfanes (formerly called sulfides), wherein the sulfur compounds are reacted in the liquid or gas phase with hydrocarbons in the presence of carbon at from 100° to 500° C.

In the novel process, aliphatic, cycloaliphatic, aromatic and araliphatic disulfanes, sulfonic acids and sulfonic acid derivatives, such as halides, e.g. chlorides or bromides, anhydrides, esters and amides, are reduced according to the general equations (a) and (b) to give thiols. The reduction of aliphatic, aromatic and araliphatic sulfones and sulfoxides takes place in accordance with equation (c) to give the sulfane.

General equations, in which R and R' are each, for example, alkyl, aryl or aralkyl:

(a)

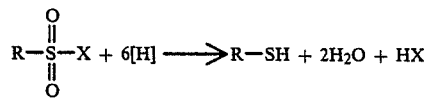

X=halogen, R'SO$_3$, R'O, NH$_2$ OH (b) R—S—S—R'+2[H]→2R—SH (c) R—SO$_n$—R'+2n[H]→R—S—R'+nH$_2$O   n=1 or 2

The hydrogen required for the reduction originates from the hydrocarbon, which is converted to derivatives having lower hydrogen contents, down to the carbon stage.

We have found, surprisingly, that very selective reduction of the stated sulfur compounds is possible at 100°-500° C. with simple paraffinic, olefinic and/or aromatic hydrocarbons and mixtures of these as hydrogen carriers.

The hydrocarbons used are, for example, high boiling mineral oil fractions whose boiling ranges are higher than the reaction temperature, which is 100°-500° C., preferably 200°-400° C., in particular 250°-350° C. Such hydrocarbons are, for example, technical grade white oil, vacuum gas oil, heavy fuel oil, vacuum residue, molten paraffin wax or aromatic hydrocarbon oil. Other suitable substances are partially hydrogenated aromatics, for example 1,2,3,4-tetrahydronaphthalene or 9,10-dihydroanthracene. However, it is also possible to use lower boiling hydrocarbons and hydrocarbon mixtures, e.g. methane, ethane, acetylene, propane, propene, butane, butene, pentane, pentene, cyclopentane, hexane, hexene, cyclohexane, etc., light fuel oil, gasoline, naphtha or liquid gas, and the reaction can be carried out either under superatmospheric pressure in the liquid phase or in the gas phase.

The hydrocarbons can advantageously be reacted in an amount of from 10 to 1,000 g, in particular from 50 to 500 g, per mole of starting material.

The reduction is carried out, according to the invention, in the presence of elemental carbon. This carbon can either be present from the outset as a constituent of the hydrocarbon used, be formed during the reaction or be added. Examples of suitable added forms of carbon are petroleum coke, carbon black or another form of graphite. Active carbons, such as Carboraffin P ® (Bayer AG Leverkusen, Federal Republic of Germany) or animal charcoal which has been activated, for example with zinc chloride, phosphoric acid or hydrogen, are particularly suitable.

The presence of elemental carbon in the reaction mixture accelerates the reaction and increases the conversion. The reaction mixture preferably contains from 1 to 50, in particular from 5 to 25, % by weight, based on the hydrocarbon, of carbon.

Sulfonyl halides, sulfonic acid anhydrides, sulfonates and sulfonamides can advantageously be used as a starting material for the preparation of thiols. In a particularly advantageous process, however, even the less reactive sulfonic acids are reduced to thiols under the reaction conditions. The reaction is applicable to aliphatic, cycloaliphatic, araliphatic and aromatic sulfonic acids and their derivatives but has particular preparative importance in the case of the aromatic members, since the corresponding intermediates are readily available by means of sulfonation reactions. In this context, another advantage is that the process provided here also readily gives aromatic dithiols; other known methods frequently lead to problems in this respect owing to side reactions, for example polymerization (cf. C. M. Suter and P. H. Scrutchfield, J. Am. Chem. Soc. 58 (1936), 54).

The novel process is also particularly suitable for the preparation of thiols from disulfanes, the latter being symmetric or asymmetric disulfanes containing aliphatic, cycloaliphatic, araliphatic or aromatic radicals. For example, aliphatic disulfanes are readily obtainable from alkyl halides and metal disulfides by nucleophilic substitution. Furthermore, the corresponding sulfanes can be prepared by conversion of symmetric or asymmetric aliphatic, araliphatic or aromatic sulfoxides and sulfones.

The organic radicals of the sulfonic acids, sulfonic acid derivatives, disulfanes, sulfoxides and sulfones can be varied widely and are not subject to any particular restrictions. Aliphatic, cycloaliphatic, araliphatic and/or aromatic radicals are, for example, alkyl, cycloalkyl, alkenyl, alkynyl, aralkyl and aryl radicals, which may carry inert substituents under the reaction conditions.

Alkyl radicals are, for example, branched or straight-chain radicals of 1 to 20, in particular 1 to 12, carbon atoms, e.g. methyl, ethyl, n-propyl, isopropyl, n-butyl, isobutyl, tert-butyl, pentyl, hexyl, octyl or dodecyl. Cycloalkyl radicals are, for example, those having from 5 to 8 ring members, in particular cyclopentyl and cyclohexyl. The group to be reduced, for example in the case of sulfolane, can itself form part of the ring. The alkyl radicals may furthermore contain double and/or triple bonds, $\alpha,\beta$-unsaturated sulfonic acids and their derivatives and $\alpha,\beta$-unsaturated sulfones and sulfoxides, however, being reduced to the corresponding saturated thiols and sulfanes. Furthermore, the alkyl radicals may carry functional groups which are inert under the reaction conditions, e.g. alkoxy, carboxyl, nitrile, amino or carbonyl groups.

The suitable aryl radicals are for example derived from the parent substances benzene, diphenyl, naphthalene, anthracene, etc. These may additionally be substituted by inert groups, such as halogen, e.g. fluorine, chlorine or bromine, alkyl, alkoxy, carboxyl, nitrile, carbonyl or amino. The aryl radicals may furthermore be hetero-aromatic groups which contain one or more nitrogen, oxygen or sulfur atoms or combinations of these. Specific examples here are heteroaromatics, such as pyrrole, pyrazole, imidazole, pyridine, pyridazine, pyrimidine, pyrazine, quinoline, isoquinoline, quinoxaline, indole, furan, oxazole, isoxazole, thiophene and thiazole.

Araliphatic radicals are, for example, those composed of the stated aliphatic and aromatic radicals. The sulfur group to be reduced may be present either in the aliphatic moiety or in the aromatic moiety. Specific examples are benzyl, phenyl ethyl and o-tolyl.

In the procedure in the liquid phase, at least a major part of the reacting hydrocarbons should be in the liquid state. The liquid phase contains suspended carbon, which is either formed during the reaction, added or present as a constituent of the hydrocarbons used, for example in heavy fuel oil or vacuum residue. If the hydrocarbon does not contain carbon from the outset, the reaction can be accelerated by adding elemental carbon to the reaction mixture.

The reaction in the liquid phase is advantageously carried out as follows: the sulfur compound to be reduced, in solid, liquid or gaseous form, if necessary together with an inert gas, e.g. nitrogen, is introduced into a suspension of carbon in a hydrocarbon which has been heated to the reaction temperature. Depending on the reaction temperature and boiling point, the reaction products leave the reaction vessel directly after the reaction and are condensed by cooling, after which they can be worked up by known methods, for example distillation. Products having a higher boiling point remain in the reaction mixture and can be isolated after the reaction in a conventional manner, for example by distillation or extraction.

In the procedure in the gas phase, the compound to be reduced, in gaseous form, is passed together with a hydrocarbon over elemental carbon as a catalyst.

The reaction can be carried out either batchwise or contihuously under atmospheric, superatmospheric or reduced pressure in the reactors usually used, for example in stirred kettles or in cylindrical reactors.

The novel process makes it possible for organic sulfur compounds, such as sulfonic acids, sulfonic acid derivatives, sulfones, sulfoxides and disulfanes to be reduced with hydrogen transfer in a cheap, technically simple manner, without the production of metal salts or salt-containing wastewaters which pollute the environment.

The Examples which follow illustrate the process without restricting it.

EXAMPLES 1 TO 6

Reduction of aromatic sulfonic acids, sulfonic acid derivatives and diphenyl disulfane 450 g of technical grade white oil and 50 g of active carbon (Carboraffin P ®) were heated to 350° C., and 0.3 mole/hour of the starting material stated in the Table below, together with 30 hour of nitrogen, were added. The starting material was added dropwise onto the surface of the stirred white oil/carbon mixture and the vapors leaving the reaction flask were condensed. Solid starting materials were melted beforehand at 90° or 140° C.

The amounts of product obtained in the condensate after an experimental time of 4 hours and the yields are shown in the Table. In the case of toluenesulfonyl chloride as the starting material, the condensate was further worked up by treating it with a 20% strength aqueous sodium hydroxide solution, acidifying the aqueous phase and extracting it with methylene chloride. After the methylene chloride had been separated off, 131.4 g of p-thiocresol were obtained, corresponding to a yield of 88.3%, based on p-toluenesulfonyl chloride.

TABLE

| Example | Starting material | Amount/h g | Product | Amount[a] g | Yield[b] % |
|---|---|---|---|---|---|
| 1 | p-$CH_3C_6H_4SO_2Cl$ | 57 | p-$CH_3$—$C_6H_4SH$ | 131.4 | 88.3 |
| 2 | p-$CH_3C_6H_4SO_3H.H_2O$ | 57 | p-$CH_3$—$C_6H_4SH$ | 124.0 | 83.3 |
| 3 | p-$CH_3C_6H_4SO_3CH_3$ | 56 | p-$CH_3$—$C_6H_4SH$ | 91.4 | 61.2 |
| 4 | $C_6H_5SO_2Cl$ | 53 | $C_6H_5SH$ | 106.8 | 80.2 |
| 5 | $C_6H_5SO_3H$ | 48 | $C_6H_5SH$ | 117.1 | 87.6 |
| 6 | $C_6H_5$—S—S—$C_6H_5$ | 66 | $C_6H_5SH$ | 263.2 | 98.8 |

[a]The amount of product obtained in the condensate after a run of 4 hours was determined by gas chromatographic analysis in Examples 2 to 6.
[b]Based on starting material used.

EXAMPLE 7

Reduction of di-n-butyldisulfane 54 g/hour (0.3 mole/hour) of di-n-butyldisulfane (melted at 90° C.) were reacted as described in Examples 1 to 6.

After an experimental time of 4 hours, a condensate was obtained which, according to gas chromatographic analysis, contained 134.5 g of 1-butanethiol in addition to 54.4 g of unconverted starting material. Accordingly, the conversion was 74.8% and the selectivity 82.3%.

EXAMPLE 8

Reduction of methanesulfonic acid 29 g/hour (0.3 mole/hour) of methanesulfonic acid were converted as described in Examples 1 to 6. The products leaving the reactor in gaseous form were condensed, initially at 0° C. and then at −78° C., and the resulting condensates investigated by gas chromatography. After an experimental time of 4 hours, 25.3 g of methanethiol were obtained in addition to 17.4 g of unconverted methanesulfonic acid. Accordingly, the conversion was 85.0% and the selectivity 51.5%.

EXAMPLE 9

Reduction of diphenyl sulfoxide 60 g/hour (0.3 mole/hour) of diphenyl sulfoxide (melted at 90° C.) were reacted as described in Examples 1 to 6.

After an experimental time of 4 hours, a condensate was obtained which, according to gas chromatographic analysis, contained 189.4 g of diphenylsulfane. This corresponded to a yield of 85.7%.

EXAMPLE 10

Reduction of dimethyl sulfoxide 23 g/hour (0.3 mole/hour) of dimethyl sulfoxide were reacted as described in Examples 1 to 6.

After an experimental time of 4 hours, a condensate was obtained which, according to gas chromatographic analysis, contained 4.4 g of unconverted dimethyl sulfoxide and 45.2 g of dimethyl sulfane. Accordingly, the conversion was 95.2% and the selectivity 64.9%.

We claim:

1. A process for the reduction of an organic sulfur compound selected from the group consisting of a sulfonic acid, sulfonyl halide, sulfonate, sulfonamide, sulfonic acid anhydride, sulfone, sulfoxide and disulfane, to form mercaptans or sulfanes which comprises:
   reacting the sulfur compound in the liquid or gas phase with a hydrocarbon in the presence of 1 to 50% by weight of elemental carbon, based on the hydrocarbon, at from 100° to 500° C.

2. A process as claimed in claim 1, wherein the hydrocarbon used is a high boiling mineral oil whose boiling point is higher than the reaction temperature.

3. A process as claimed in claim 1, wherein the hydrocarbon used is a vacuum residue, heavy fuel oil or technical grade white oil.

4. A process as claimed in claim 1, wherein the reaction is carried out with a low boiling hydrocarbon, selected from the group consisting of light fuel oil, gasoline, naphtha, ethane, propane and butane in the gas phase or under superatmospheric pressure in the liquid phase.

5. A process as claimed in claim 1 wherein the carbon is used in an amount of from 5 to 25% by weight, based on the hydrocarbon.

6. A process as claimed in claim 1, wherein the carbon used is activated carbon.

7. A process as claimed in claim 1, wherein a sulfonic acid, sulfonyl halide, sulfonamide or sulfonic acid anhydride is reduced to a thiol.

8. A process as claimed in claim 1, wherein a disulfane is reduced to a thiol.

9. A process as claimed in claim 1, wherein a sulfone or sulfoxide is reduced to a sulfane.

10. A process as claimed in claim 1, wherein the hydrocarbon is reacted in an amount of from 10 to 1,000 g per mole of the starting sulfur compound.

11. A process as claimed in claim 1, wherein the hydrocarbon is reacted in an amount of from 50 to 500 g per mole of the starting sulfur compound.

12. A process as claimed in claim 1, wherein the reaction temperature is 200° to 400° C.

13. A process as claimed in claim 1, wherein the reaction temperature is 250° to 350° C.

14. A process as claimed in claim 1, wherein the reaction is carried out in the liquid phase with at least a major part of the hydrocarbon being in the liquid state and the elemental carbon being suspended in the liquid phase.

* * * * *